(12) United States Patent
Jung et al.

(10) Patent No.: US 11,998,648 B2
(45) Date of Patent: Jun. 4, 2024

(54) STERILIZATION MODULE

(71) Applicant: SEOUL VIOSYS CO., LTD., Gyeonggi-do (KR)

(72) Inventors: Woong Ki Jung, Gyeonggi-do (KR); Ji Hyun Jo, Gyeonggi-do (KR); Byeong Cheol Ju, Gyeonggi-do (KR); Jae Young Choi, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 418 days.

(21) Appl. No.: 17/352,754

(22) Filed: Jun. 21, 2021

(65) Prior Publication Data
US 2021/0308307 A1 Oct. 7, 2021

Related U.S. Application Data

(63) Continuation of application No. PCT/KR2019/018058, filed on Dec. 19, 2019.

(30) Foreign Application Priority Data

Dec. 21, 2018 (KR) .......................... 10-2018-0167533

(51) Int. Cl.
*A61L 2/10* (2006.01)
*A61L 2/26* (2006.01)

(52) U.S. Cl.
CPC ........ *A61L 2/10* (2013.01); *A61L 2/26* (2013.01); *A61L 2202/11* (2013.01)

(58) Field of Classification Search
CPC ..... A61L 2/10; A61L 2/26; A61L 2/08; A61L 2/084; A61L 2202/11; A61L 2202/121

USPC ............................ 250/504 R, 453.11, 455.11
See application file for complete search history.

(56) References Cited

U.S. PATENT DOCUMENTS

| | | | |
|---|---|---|---|
| 2006/0108594 A1* | 5/2006 | Iwasaki | H01L 33/58 257/E33.073 |
| 2009/0035176 A1* | 2/2009 | Normark | A61L 2/10 422/4 |
| 2017/0073048 A1* | 3/2017 | Butcher | F21V 23/001 |

FOREIGN PATENT DOCUMENTS

| CN | 204834683 U | 12/2015 |
|---|---|---|
| CN | 205892799 U | 1/2017 |
| CN | 207979518 | 10/2018 |
| JP | 08-129343 A | 5/1996 |

(Continued)

OTHER PUBLICATIONS

International Search Report for International Application PCT/KR2019/018058, dated Apr. 6, 2020.

(Continued)

*Primary Examiner* — Jason L McCormack
(74) *Attorney, Agent, or Firm* — Perkins Coie LLP

(57) ABSTRACT

A sterilization module includes a main body having an opening on the top surface thereof, a transparent member which is arranged on the inside of the main body so as to cover the opening, and through which light passes, an inner sealing member which is made of an elastic material and which covers the side surface of the transparent member, a light emitting module that comprises a substrate and a light emitting element installed on the upper surface of the substrate, and which emits light through the transparent member, and an inner holder which is fastened to the inner side surface of the main body and fixes the light emitting module to the inside of the main body.

8 Claims, 8 Drawing Sheets

(56) References Cited

FOREIGN PATENT DOCUMENTS

| KR | 20020013885 A | 2/2002 |
|---|---|---|
| KR | 1020130143281 | 12/2013 |
| KR | 101691597 | 1/2017 |
| KR | 101887621 | 9/2018 |
| KR | 1020180130822 | 12/2018 |
| WO | 2018084244 A1 | 5/2018 |
| WO | 2018111056 A1 | 6/2018 |

OTHER PUBLICATIONS

Extended / Supplementary Search Report issued in corresponding EP Application No. 19899092.1, dated Aug. 11, 2022, 8 pages.
Office Action from corresponding Korean Patent Application No. 10-2018-0167533, dated Nov. 15, 2023 (11 pages).
English translation of Chinese Office Action from corresponding Chinese Patent Application No. 201980003298.2 dated Nov. 2, 2022.

* cited by examiner

STERILIZATION MODULE

CROSS-REFERENCE OF RELATED APPLICATIONS AND PRIORITY

The Present Application is a continuation of International Patent Application No. PCT/KR2019/018058 filed Dec. 19, 2019, which claims priority to and benefit of Korean Patent Application No. 10-2018-0167533 filed Dec. 21, 2018, the disclosure of which are incorporated herein by reference in their entirety.

TECHNICAL FIELD

Embodiments of the present disclosure relate to a sterilization module.

BACKGROUND

Ultraviolet (UV) light has different properties depending on wavelength thereof and such properties of the UV light are used by sterilization apparatuses. In general, a UV-based sterilization apparatus employs a mercury (Hg) lamp. Ozone ($O_3$) produced by UV wavelengths emitted from the mercury lamp has germicidal efficacy. However, the mercury (Hg) lamp can cause environmental problems over time due to mercury contained therein.

In recent years, sterilization apparatuses using various types of UV light have been developed and put into use. In addition, sterilizing objects are also diversifying. Such a sterilization apparatus is embedded in a specific device, such as a refrigerator, a washing machine, a humidifier, and a water purifier.

SUMMARY

Embodiments of the present disclosure provide a sterilization module that can reduce damage to a substrate of a light emitting module.

Embodiments of the present disclosure provide a sterilization module that can ensure uniform coupling force between internal components from product to product, thereby improving product reliability.

Embodiments of the present disclosure provide a sterilization module that can ensure easy and damage-free assembly.

In accordance with one aspect of the present disclosure, a sterilization module includes a main body including an opening formed through an upper surface thereof, a light-transmissive member disposed inside the main body to cover the opening and transmitting light therethrough; an inner sealing member surrounding a side surface of the light-transmissive member and formed of an elastic material, a light emitting module including a substrate and a light emitting device mounted on an upper surface of the substrate, the light emitting module emitting light to the light-transmissive member, and an inner holder fastened to an inner side surface of the main body and holding the light emitting module inside the main body.

In at least one variant, the inner sealing member has an upper surface held against the upper surface of the main body and a lower surface held against an upper surface of the substrate of the light emitting module. In addition, the light-transmissive member is spaced apart from the substrate by a distance allowing an irradiance of light emitted to an outside of the sterilization module through the light-transmissive member to be 65% or more of an irradiance of light emitted from the light emitting device.

In another variant, the sterilization module further includes: a fastening groove formed on the inner side surface of the main body; and a coupling portion formed on an outer side surface of the inner holder, wherein the inner holder is fastened and secured to the main body through insertion of the coupling portion into the fastening groove.

In further another variant, the main body further includes a groove-shaped fastening guide formed on a portion of the inner side surface thereof, the fastening guide being connected at one end thereof to a lower surface of the main body and connected at the other end thereof to the fastening groove, and the coupling portion of the inner holder is inserted into the fastening guide of the main body and is moved along the fastening guide until the coupling portion is inserted into the fastening groove.

In another variant, the main body further includes a fastening guide formed on a portion of the inner side surface thereof and having elasticity, the fastening guide being connected at one end thereof to a lower surface of the main body and connected at the other end thereof to the fastening groove, and the coupling portion of the inner holder is moved along the fastening guide until the coupling portion is inserted into the fastening groove.

In another variant, a distance from an inner upper surface of the main body to an upper end of the fastening groove is less than the sum of a distance from the upper surface of the inner sealing member to the lower surface of the inner sealing member, a distance from the upper surface of the substrate to a lower surface of the substrate, and a distance from an upper surface of the inner holder to an upper end of the coupling portion.

In another variant, an upper surface of the inner holder has a smaller width than a lower surface of the inner holder, the width being a distance from an inner side surface of the inner holder to an outer side surface of the inner holder, and the upper surface of the inner holder faces a lower surface of the substrate.

In another variant, the sterilization module further includes; a buffer member covering the upper surface of the inner holder.

In another variant, the inner sealing member further comprises a protrusion formed around a lower outer surface thereof, the main body further includes an insertion groove formed the inner side surface thereof, and the protrusion of the inner sealing member is inserted into the insertion groove of the main body.

In accordance with another aspect of the present disclosure, a sterilization module includes a main body including an opening formed through an upper surface thereof, a light-transmissive member disposed inside the main body to cover the opening and transmitting light therethrough, an inner sealing member formed on an inner side surface thereof with a light-transmissive member mounting groove into which a side surface of the light-transmissive member is inserted, the inner sealing member being formed of an elastic material, a light emitting module including a substrate and a light emitting device mounted on an upper surface of the substrate, the light emitting module emitting light to the light-transmissive member, and an inner holder fastened to an inner side surface of the main body and holding the light emitting module inside the main body.

In at least one variant, the light-transmissive member is mounted on the inner sealing member through insertion of the side surface of the light-transmissive member into the light-transmissive member mounting groove, and a distance from a lower surface of the inner sealing member to a lower end of the light-transmissive member mounting groove is greater than a distance from an upper surface of the inner sealing member to an upper end of the light-transmissive member mounting groove.

In another variant, the sterilization module further includes a fastening groove formed on the inner side surface of the main body, and a coupling portion formed on an outer side surface of the inner holder. The inner holder is fastened and secured to the main body through insertion of the coupling portion into the fastening groove.

In another variant, the main body further includes a groove-shaped fastening guide formed on a portion of the inner side surface thereof, the fastening guide being connected at one end thereof to a lower surface of the main body and connected at the other end thereof to the fastening groove, and the coupling portion of the inner holder is inserted into the fastening guide of the main body and is moved along the fastening guide until the coupling portion is inserted into the fastening groove.

In further another variant, the main body further includes a fastening guide formed on a portion of the inner side surface thereof and having elasticity, the fastening guide being connected at one end thereof to a lower surface of the main body and connected at the other end thereof to the fastening groove, and the coupling portion of the inner holder is moved along the fastening guide until the coupling portion is inserted into the fastening groove.

In another variant, a distance from an inner upper surface of the main body to an upper end of the fastening groove is less than the sum of a distance from the upper surface of the inner sealing member to the lower surface of the inner sealing member, a distance from the upper surface of the substrate to a lower surface of the substrate, and a distance from an upper surface of the inner holder to an upper end of the coupling portion.

In another variant, an upper surface of the inner holder has a smaller width than a lower surface of the inner holder, the width being a distance from an inner side surface of the inner holder to an outer side surface of the inner holder, and the upper surface of the inner holder faces a lower surface of the substrate.

In another variant, the sterilization module further includes: a buffer member covering an upper surface of the inner holder.

In another variant, the inner sealing member further includes a protrusion formed around a lower outer side surface thereof.

In another variant, the main body further includes an insertion groove formed around the inner side surface thereof, and the protrusion of the inner sealing member is inserted into the insertion groove of the main body.

In accordance with a further aspect of the present disclosure, a sterilization module includes a main body including an opening formed through an upper surface thereof, a light-transmissive member disposed inside the main body to cover the opening and transmitting light therethrough, an inner sealing member surrounding a side surface of the light-transmissive member and formed of an elastic material, a light emitting module including a substrate and a light emitting device mounted on an upper surface of the substrate, the light emitting module emitting light to the light-transmissive member, and an inner holder fastened to an inner side surface of the main body and holding the light emitting module inside the main body.

In at least one variant, the inner sealing member has an upper surface held against the upper surface of the main body and a lower surface held against an upper surface of the substrate of the light emitting module, an upper surface of the inner holder faces a lower surface of the substrate, and the upper surface of the inner holder has a smaller width than a lower surface of the inner holder, the width being a distance from an inner side surface of the inner holder to an outer side surface of the inner holder.

In another variant, the sterilization module further includes: a fastening groove formed on the inner side surface of the main body; and a coupling portion formed on the outer side surface of the inner holder, wherein the inner holder is fastened and secured to the main body through insertion of the coupling portion into the fastening groove.

In another variant, a distance from an inner upper surface of the main body to an upper end of the fastening groove is less than the sum of a distance from the upper surface of the inner sealing member to the lower surface of the inner sealing member, a distance from the upper surface of the substrate to the lower surface of the substrate, and a distance from the upper surface of the inner holder to an upper end of the coupling portion.

In another variant, the light-transmissive member is formed on an inner side surface thereof with a light-transmissive member mounting groove into which the side surface of the light-transmissive member is inserted, and a distance from the lower surface of the inner sealing member to a lower end of the light-transmissive member mounting groove is greater than a distance from the upper surface of the inner sealing member to an upper end of the light-transmissive member mounting groove.

In another variant, a distance from an inner upper surface of the main body to an upper end of the fastening groove is less than a sum of a height the inner sealing member, a thickness of the substrate, and a distance from an upper surface of the inner holder to an upper end of the coupling portion.

In another variant, an upper surface of the inner holder has a smaller area than an area of a lower surface of the inner holder and the upper surface of the inner holder faces a lower surface of the substrate.

The sterilization module according to embodiments of the present disclosure can reduce damage to the substrate through reduction in contact area between the substrate and the inner holder adapted to press and secure the substrate.

Additionally or alternatively, the sterilization module according to embodiments of the present disclosure can reduce damage to the substrate through increase in contact area between the substrate and the inner sealing member.

Further, the sterilization module according to embodiments of the present disclosure can ensure uniform coupling force between the main body and the inner holder from product to product, thereby improving product reliability.

Furthermore, with the fastening guide formed on the inner side surface of the main body and connected to the fastening groove, the sterilization module according to embodiments of the present disclosure can ensure damage-free coupling between the inner holder and the main body.

DESCRIPTION OF DRAWINGS

FIG. 1 illustrates a perspective view of the sterilization module according to the first embodiment of the present disclosure;

FIG. 2 illustrates an exploded view of the sterilization module of FIG. 1; and

FIG. 3 illustrates a sectional view of the sterilization module of FIG. 1.

FIG. 6 illustrates an exploded view of a sterilization module according to a fourth embodiment of the present disclosure; and FIG. 7 illustrates a sectional view of the sterilization module of FIG. 6;

FIG. 9 illustrates a sectional view of a main body of a sterilization module; and FIG. 10 illustrates a sectional view of the sterilization module.

FIG. 11 illustrates a sectional view of a main body of a sterilization module; and FIG. 12 illustrates a sectional view of the sterilization module.

DETAILED DESCRIPTION OF EMBODIMENTS

Figure 1:
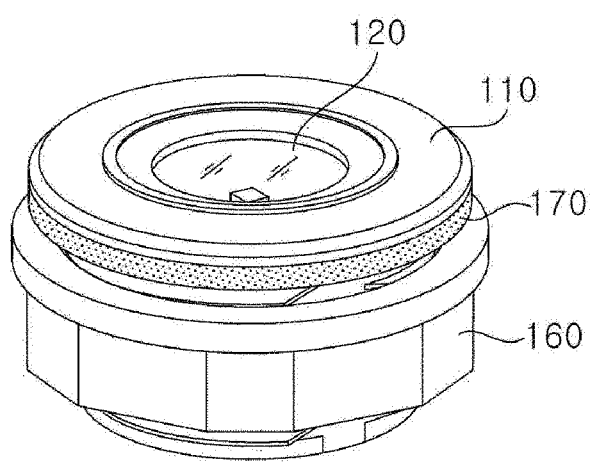
FIG. 1 to FIG. 3 are exemplary views of a sterilization module according to a first embodiment of the present disclosure, where.

Hereinafter, embodiments of the present disclosure will be described with reference to the accompanying drawings. It should be understood that the embodiments are provided for complete disclosure and thorough understanding of the present disclosure by those skilled in the art. Therefore, the present disclosure is not limited to the following embodiments and may be embodied in different ways. In addition, the drawings may be exaggerated in width, length, and thickness of components for descriptive convenience and clarity only. Like components will be denoted by like reference numerals throughout the specification.

One aspect of the present disclosure relates to a sterilization module including a main body including an opening formed through an upper surface thereof and a fastening groove formed an inner side surface thereof, a light-transmissive member disposed inside the main body to cover the opening and transmitting light therethrough, an inner sealing member surrounding a side surface of the light-transmissive member and formed of an elastic material, a light emitting module including a substrate and a light emitting device mounted on an upper surface of the substrate, the light emitting module emitting light to the light-transmissive member, and an inner holder fastened to the inner side surface of the main body and holding the light emitting module inside the main body.

In at least one variant, the inner sealing member has an upper surface held against the upper surface of the main body and a lower surface held against an upper surface of the substrate of the light emitting module. In addition, the light-transmissive member is spaced apart from the substrate by a distance allowing an irradiance of light emitted to an outside of the sterilization module through the light-transmissive member to be 65% or more of an irradiance of light emitted from the light emitting device.

In another variant, the sterilization module further includes a fastening groove formed on the inner side surface of the main body, and a coupling portion formed on an outer side surface of the inner holder. The inner holder is fastened and secured to the main body through insertion of the coupling portion into the fastening groove.

In another variant, the main body further includes a groove-shaped fastening guide formed on a portion of the inner side surface thereof, the fastening guide being connected at one end thereof to a lower surface of the main body and connected at the other end thereof to the fastening groove, and the coupling portion of the inner holder is inserted into the fastening guide of the main body and is moved along the fastening guide until the coupling portion is inserted into the fastening groove.

In another variant, the main body further includes a fastening guide formed on a portion of the inner side surface thereof and having elasticity, the fastening guide being connected at one end thereof to a lower surface of the main body and connected at the other end thereof to the fastening groove, and the coupling portion of the inner holder is moved along the fastening guide until the coupling portion is inserted into the fastening groove.

In another variant, a distance from an inner upper surface of the main body to an upper end of the fastening groove is less than the sum of a distance from the upper surface of the inner sealing member to the lower surface of the inner sealing member, a distance from the upper surface of the substrate to a lower surface of the substrate, and a distance from an upper surface of the inner holder to an upper end of the coupling portion.

In another variant, an upper surface of the inner holder has a smaller width than a lower surface of the inner holder, the width being a distance from an inner side surface of the inner holder to an outer side surface of the inner holder, and the upper surface of the inner holder faces a lower surface of the substrate.

In another variant, the sterilization module further includes a buffer member covering the upper surface of the inner holder.

In another variant, the inner sealing member further comprises a protrusion formed around a lower outer surface thereof, the main body further includes an insertion groove formed the inner side surface thereof, and the protrusion of the inner sealing member is inserted into the insertion groove of the main body.

Another aspect of the present disclosure relates to a sterilization module including: a main body including an opening formed through an upper surface thereof and a fastening groove formed an inner side surface thereof; a light-transmissive member disposed inside the main body to cover the opening and transmitting light therethrough; an inner sealing member formed on an inner side surface thereof with a light-transmissive member mounting groove into which a side surface of the light-transmissive member is inserted, the inner sealing member being formed of an elastic material, a light emitting module including a substrate and a light emitting device mounted on an upper surface of the substrate, the light emitting module emitting light to the light-transmissive member, and an inner holder fastened to the inner side surface of the main body and holding the light emitting module inside the main body.

In at least one variant, the light-transmissive member is mounted on the inner sealing member through insertion of the side surface of the light-transmissive member into the light-transmissive member mounting groove, and a distance from a lower surface of the inner sealing member to a lower end of the light-transmissive member mounting groove is greater than a distance from an upper surface of the inner sealing member to an upper end of the light-transmissive member mounting groove.

In another variant, the sterilization module further includes a fastening groove formed on the inner side surface of the main body; and a coupling portion formed on an outer side surface of the inner holder, wherein the inner holder is fastened and secured to the main body through insertion of the coupling portion into the fastening groove.

In another variant, the main body further includes a groove-shaped fastening guide formed on a portion of the inner side surface thereof, the fastening guide being connected at one end thereof to a lower surface of the main body and connected at the other end thereof to the fastening groove, and the coupling portion of the inner holder is inserted into the fastening guide of the main body and is moved along the fastening guide until the coupling portion is inserted into the fastening groove.

In another variant, the main body further includes a fastening guide formed on a portion of the inner side surface thereof and having elasticity, the fastening guide being connected at one end thereof to a lower surface of the main body and connected at the other end thereof to the fastening groove, and the coupling portion of the inner holder is moved along the fastening guide until the coupling portion is inserted into the fastening groove.

A distance from an inner upper surface of the main body to an upper end of the fastening groove is less than the sum of a distance from the upper surface of the inner sealing member to the lower surface of the inner sealing member, a distance from the upper surface of the substrate to a lower surface of the substrate, and a distance from an upper surface of the inner holder to an upper end of the coupling portion.

In another variant, an upper surface of the inner holder has a smaller width than a lower surface of the inner holder, the width being a distance from an inner side surface of the inner holder to an outer side surface of the inner holder, and the upper surface of the inner holder faces a lower surface of the substrate.

In another variant, the sterilization module further includes: a buffer member covering an upper surface of the inner holder.

In another variant, the inner sealing member further includes a protrusion formed around a lower outer surface thereof.

In another variant, the main body further includes an insertion groove formed around the inner side surface thereof, and the protrusion of the inner sealing member is inserted into the insertion groove of the main body.

A further aspect of the present disclosure relates to a sterilization module includes a main body including an opening formed through an upper surface thereof and a fastening groove formed an inner side surface thereof, a light-transmissive member disposed inside the main body to cover the opening and transmitting light therethrough, an inner sealing member surrounding a side surface of the light-transmissive member and formed of an elastic material, a light emitting module including a substrate and a light emitting device mounted on an upper surface of the substrate, the light emitting module emitting light to the light-transmissive member, and an inner holder fastened to the inner side surface of the main body and holding the light emitting module inside the main body.

In another variant, the inner sealing member has an upper surface held against the upper surface of the main body and a lower surface held against an upper surface of the substrate of the light emitting module, an upper surface of the inner holder faces a lower surface of the substrate, and the upper surface of the inner holder has a smaller width than a lower surface of the inner holder, the width being a distance from an inner side surface of the inner holder to an outer side surface of the inner holder.

In another variant, the sterilization module further includes: a fastening groove formed on the inner side surface of the main body; and a coupling portion formed on the outer side surface of the inner holder, wherein the inner holder is fastened and secured to the main body through insertion of the coupling portion into the fastening groove.

A distance from an inner upper surface of the main body to an upper end of the fastening groove is less than the sum of a distance from the upper surface of the inner sealing member to the lower surface of the inner sealing member, a distance from the upper surface of the substrate to the lower surface of the substrate, and a distance from the upper surface of the inner holder to an upper end of the coupling portion.

A distance from the lower surface of the inner sealing member to a lower end of the light-transmissive member mounting groove is greater than a distance from the upper surface of the inner sealing member to an upper end of the light-transmissive member mounting groove.

Figure 2:
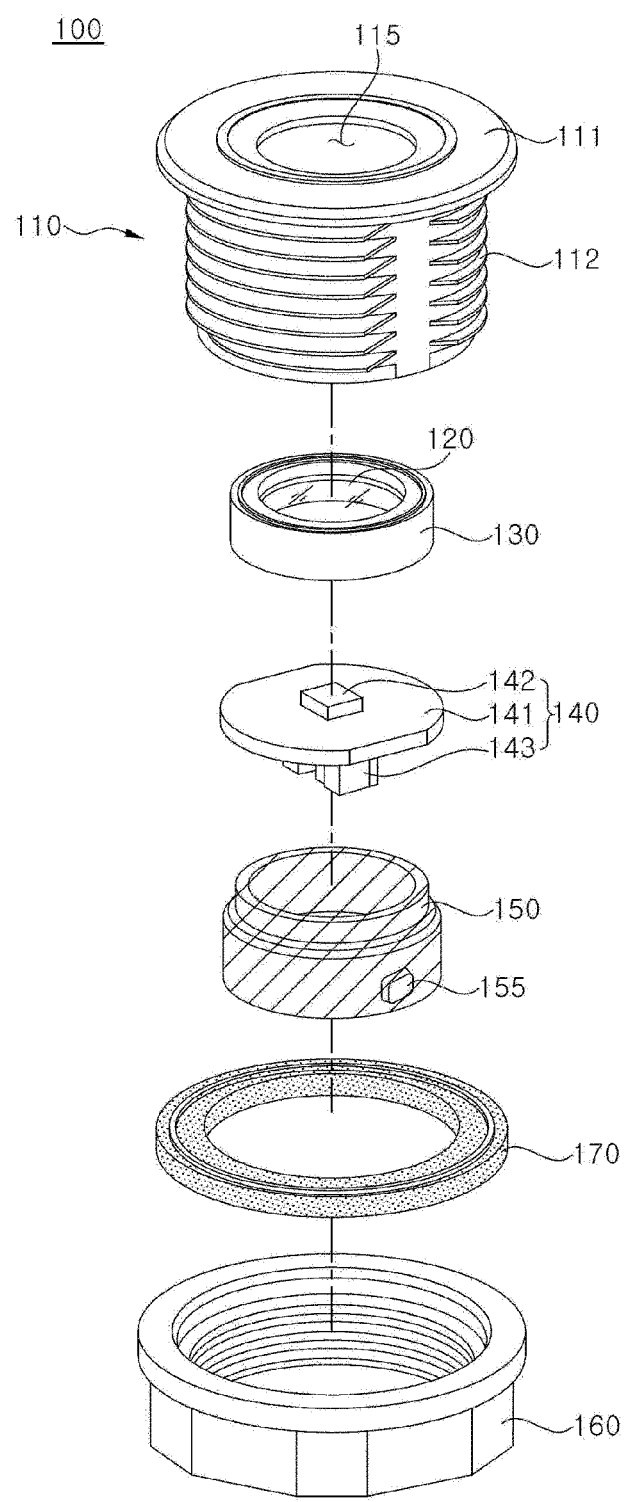
Figure 3:
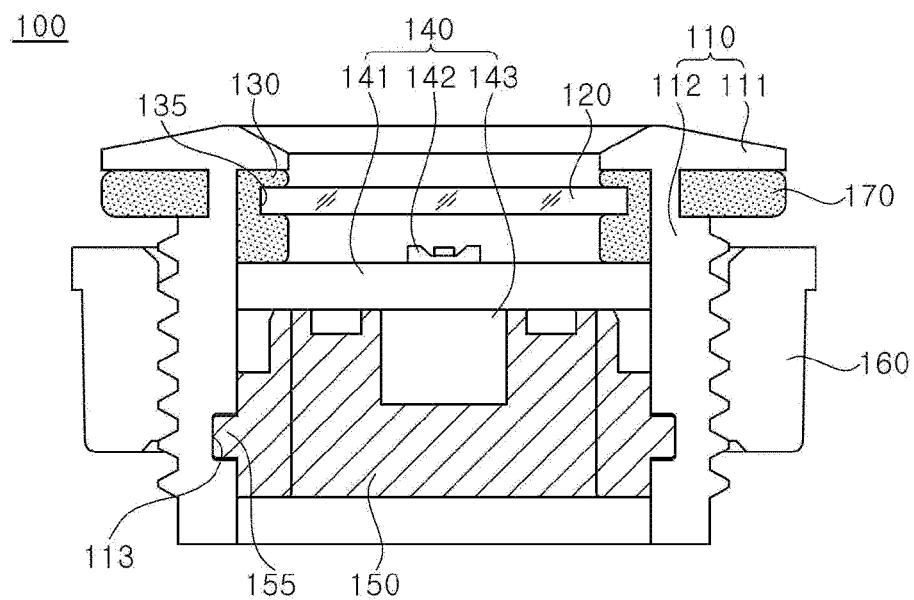

FIG. 1 to FIG. 3 are exemplary views of a sterilization module according to a first embodiment of the present disclosure.

FIG. 1 is a perspective view of the sterilization module according to the first embodiment of the present disclosure. FIG. 2 is an exploded view of the sterilization module according to the first embodiment of the present disclosure. FIG. 3 is a sectional view of the sterilization module according to the first embodiment of the present disclosure.

Referring to FIG. 1 to FIG. 3, the sterilization module 100 according to the first embodiment includes a main body 110, a light-transmissive member 120, an inner sealing member 130, a light emitting module 140, and an inner holder 150, an outer holder 160, and an outer sealing member 170.

According to this embodiment of the present disclosure, the main body 110 has an inner space defined by an upper surface 111 and a side surface 112. That is, the main body 110 is open at a bottom thereof. In addition, the main body 110 is adapted to house the light-transmissive member 120, the inner sealing member 130, the light emitting module 140, and the inner holder 150 therein.

The main body 110 includes an opening 115 formed through the upper surface 111. The opening 115 is a passage through which light from the light emitting module 140 exits the main body 110. According to this embodiment, the inner space of the main body 110 has a larger cross-sectional area than the opening and a smaller cross-sectional area than the upper surface 111. For example, when the opening 115 and the inner space have a circular cross-section, the inner space has a larger diameter than the opening 115 and a smaller diameter than a rim of the upper surface 111. In addition, the rim of the upper surface 111 of the main body 110 protrudes farther outward than the side surface 112.

The main body 110 includes a fastening groove 113 for coupling the inner holder 150 to the main body 110. The fastening groove 113 is formed on an inner side surface of the main body 110. The main body 110 is fastened to the inner holder 150 through insertion of a coupling portion 155 of the inner holder 150 into the fastening groove 113.

The light-transmissive member 120 is disposed inside of the main body 110 and covers the opening 115. The light-transmissive member 120 is formed of a material permeable to germicidal light emitted from the light emitting module 140. For example, the light-transmissive member 120 may be formed of at least one selected from among quartz, a poly(methyl methacrylate) (PMMA) resin, and a fluorine-based polymer resin.

The inner sealing member 130 secures the light-transmissive member 120 such that the light-transmissive member 120 is located under the opening 115 of the main body 110. In addition, the inner sealing member 130 separates the light-transmissive member 120 from the light emitting module 140.

The inner sealing member 130 is open at a top and bottom thereof. In addition, the inner sealing member 130 includes a light-transmissive member mounting groove 135 formed along an inner peripheral surface thereof.

The light-transmissive member mounting groove 135 is adapted to insert a side surface of the light-transmissive member 120 thereinto. That is, the light-transmissive member 120 is mounted on the light-transmissive member mounting groove 135 to be secured inside the inner sealing member 130. In addition, the inner sealing member 130 surrounds the side surface of the light-transmissive member 120.

The inner sealing member 130 with the light-transmissive member 120 mounted thereon is disposed between the main body 110 and the light emitting module 140. With the main body 110 fastened to the inner holder 150, the inner sealing member 130 is held against both the upper surface 111 of the main body 110 and a substrate 141 of the light emitting module 140. More specifically, an upper surface of the inner sealing member 130 is held against the upper surface 111 between the opening 115 and the side surface 112 of the main body 110. In addition, a lower surface of the inner sealing member 130 is held against an upper surface of the substrate 141.

According to this embodiment, a length of a lower portion of the inner sealing member 130 is greater than a length of an upper portion of the inner sealing member 130. Here, the length of the upper portion of the inner sealing member 130 is a distance from the upper surface of the inner sealing member 130 to an upper end of the light-transmissive member mounting groove 135. In addition, the length of the lower portion of the inner sealing member 130 is a distance from the lower surface of the inner sealing member 130 to a lower end of the light-transmissive member mounting groove 135.

Since the light-transmissive member 120 is mounted inside the inner sealing member 130, the length of the lower portion of the inner sealing member 130 corresponds to a distance between the light-transmissive member 120 and the substrate 141.

A luminous efficiency of the sterilization module 100 may vary depending on a distance between the light-transmissive member 120 and a light emitting device 142 mounted on the substrate 141. According to this embodiment, the substrate 141 is spaced apart from the light-transmissive member 120 by a predetermined distance, allowing the sterilization module 100 to have a luminous efficiency of 65% or more. That is, the length of the lower portion of the inner sealing member 130 is set to a degree allowing the sterilization module 100 to have a luminous efficiency of 65% or more.

The inner sealing member 130 is formed of an elastic material. For example, the inner sealing member 130 may be formed of rubber. Accordingly, the inner sealing member 130 can protect the light-transmissive member 120 from external impact through absorption of external impact energy.

The light emitting module 140 is disposed between the light-transmissive member 120 and the inner holder 150 and emits germicidal light toward the light-transmissive member 120.

The light emitting module 140 includes the substrate 141 and the light emitting device 142.

The light emitting device 142 is mounted on the upper surface of the substrate 141. For example, the light emitting device 142 is a light emitting diode package including a light emitting diode.

The light emitting device 142 emits germicidal light, that is, light capable of killing germs. For example, the germicidal light may be UV light. However, it will be understood that the germicidal light is not limited to UV light and may be visible light capable of killing germs.

The substrate 141 is electrically connected to the light emitting device 142 to supply power to the light emitting device 142. The substrate 141 may be of any type so long as the substrate can be electrically connected to the light emitting device 142. For example, the substrate 141 may be a substrate with an interconnect formed thereon, such as a printed circuit substrate, a metal substrate, and a ceramic substrate.

The light emitting module 140 may further include at least one component 143, such as a connector, a diode chip, and the like. The component 143 may be disposed on a lower surface of the substrate 141.

The inner holder 150 is fastened to the main body 110 to secure the light emitting module 140 and the inner sealing member 130 inside the main body 110.

The inner holder 150 includes the coupling portion 155 for coupling the inner holder 150 to the main body 110.

The coupling portion 155 protrudes from an outer side surface of the inner holder 150. The main body 110 is fastened to the inner holder 150 by inserting the coupling portion 155 into the fastening groove 113 of the main body 110 with the inner holder 150 received in the main body 110. That is, the inner holder 150 is secured inside the main body 110 through insertion of the coupling portion 155 into the fastening groove 113.

With the inner holder 150 fastened to the main body 110, an upper surface of the inner holder 150 is held against the lower surface of the substrate 141 of the light emitting module 140.

In conventional sterilization modules, a light emitting module is secured inside a main body by screw fastening.

However, since force to tighten a screw varies from person to person, screw fastening, which is performed by hand, can cause coupling force between the light emitting module and the main body to vary from product to product. If coupling force between the light emitting module and the main body is insufficient, the light emitting module can be easily decoupled from the main body even with a small external impact, causing reduction in product reliability. Then, the light emitting module can escape from the sterilization module or can be moved from a predetermined position, causing reduction in luminous efficiency of the sterilization module.

In the sterilization module 100 according to this embodiment, the fastening groove 113 of the main body 110 and the coupling portion 155 of the inner holder 150 are fastened to each other at a predetermined position. Accordingly, the sterilization module 100 according to this embodiment can ensure uniform coupling force between the main body 110 and the inner holder 150 from product to product. In addition, the sterilization module 100 according to this embodiment can have improved reliability through maintenance of constant coupling force between the main body 110 and the inner holder 150.

When fastened to the main body 110, the inner holder 150 needs to be able to withstand coupling force applied thereto. In addition, when fastened to the main body 110, the inner holder 150 needs to be able to prevent the substrate 141 from being damaged by force applied to the substrate 141 by the inner holder 150 pressed against the substrate 141.

Accordingly, a lower portion of the inner holder 150, which is formed with the coupling portion 155 fastened to the main body 110, has a different thickness than an upper portion of the inner holder 150, which is held against the substrate 141. According to this embodiment, the upper surface of the inner holder 150 has a smaller width than the lower surface of the inner holder 150. Here, the width is a distance from an inner side surface of the inner holder 150 to an outer side surface of the inner holder 150. That is, the side surface of the inner holder 150 has a smaller thickness at an upper portion thereof than a lower portion thereof.

Since the upper surface of the inner holder 150 has a relatively narrow width as compared with the lower surface of the inner holder 150, contact between the inner holder 150 and the substrate 141 occurs over a small area. Accordingly, it is possible to reduce an area over which force from the inner holder 150 is applied to the substrate 141 with the inner holder 150 fastened to the main body 110. As a result, it is possible to minimize damage to the substrate 141, such as warpage or breakage of the substrate 141 due to pressing force of the inner holder 150 against the substrate 141.

In addition, since the upper surface of the inner holder 150 has a relatively narrow width, it is possible to minimize errors due to various factors that may occur during production of the inner holder 150. For example, the errors may include increase in slope of the upper surface of the inner holder 150. Such an error can increase a contact area between the inner holder 150 and the substrate 141, causing increase in area over which the substrate 141 is pressed by the inner holder 150. In addition, a portion of the substrate 141 held against the inner holder 150 can suffer warpage depending on slope of the upper surface of the inner holder 150.

According to this embodiment, it is possible to reduce process factor-induced errors causing damage to the substrate 141 through reduction in width of the upper surface of the inner holder 150.

As described above, the lower surface of the inner holder 150 has a relatively large width, as compared with the upper surface of the inner holder 150. That is, the side surface of the inner holder 150 has a larger thickness at the lower portion thereof than at the upper portion thereof.

If the lower portion of the side surface of the inner holder 150 is excessively thin, the inner holder 150 can be warped or broken by force applied thereto upon coupling the inner holder 150 to the main body 110. Accordingly, the lower portion of the side surface of the inner holder 150 is designed to have a larger thickness than the upper portion of the side surface of the inner holder 150 in consideration of coupling strength of the inner holder 150 with respect to the main body 110.

In the sterilization module 100 according to this embodiment, a distance from the upper surface of the inner sealing member 130 to an upper end of the coupling portion 155 of the inner holder 150 is greater than a distance from an inner upper surface of the main body 110 to an upper end of the fastening groove 113. Here, the distance from the upper surface of the inner sealing member 130 to the upper end of the coupling portion 155 of the inner holder 150 refers to a distance by which the inner upper surface of the main body 110 is spaced apart from the upper end of the fastening groove before coupling the inner holder 150 to the main body 110.

In addition, the distance from the upper surface of the inner sealing member 130 to the upper end of the coupling portion 155 of the inner holder 150 is set to a degree allowing the inner holder 150 to be fastened to the main body 110 through compression of the inner sealing member 130.

Due to this structure, the inner holder 150 presses the substrate 141 from below upon coupling the inner holder 150 to the main body 110. Then, the inner sealing member 130 disposed between the upper surface 111 of the main body 110 and the substrate 141 is elastically compressed. In this way, the inner sealing member 130 can be firmly held against the main body 110. Accordingly, the sterilization module 100 according to this embodiment can ensure tight sealing of a gap between the opening 115 of the main body 110 and the inner sealing member 130 or the light-transmissive member 120. Through tight sealing of the opening 115 of the sterilization module 100, it is possible to prevent intrusion of moisture or dust into the sterilization module 100 through the opening 115. That is, the sterilization module 100 can have improved waterproofness and dust-proofness.

Further, due to this structure, the substrate 141 is firmly held against the inner sealing member 130 and the inner holder 150. Accordingly, the substrate 141 is stably secured inside the sterilization module 100 and thus can be prevented from shaking or moving from a predetermined position when an impact is applied to the sterilization module 100.

The sterilization module 100 may further include the outer holder 160.

The main body 110 may be secured to an enclosure with a sterilization target placed therein through coupling to the outer holder 160. The main body 110 is fastened to the outer holder 160 with the side surface 112 received in the outer holder 160.

For example, the main body 110 may be secured to an enclosure with a sterilization target placed therein such that the upper surface 111 is located inside the enclosure with the side surface 112 passing through one surface of the enclosure. Here, the outer holder 160 may be fastened to the side surface 112 of the main body 110 to be held against the one surface of the enclosure from the outside of the enclosure. In this way, the sterilization module 100 can be secured to the enclosure with the sterilization target placed therein through coupling between the main body 110 and the outer holder 160.

According to this embodiment, each of an outer side surface of the main body 110 and an inner side surface of the outer holder 160 is formed with a thread. The main body 110 is fastened to the outer holder 160 by inserting the side surface 112 of the main body 110 into the outer holder and engaging the thread on the outer side surface of the main body 110 with the thread on the inner side surface of the outer holder 160.

The sterilization module 100 may further include the outer sealing member 170.

The outer sealing member 170 is formed of an elastic material. For example, the outer sealing member 170 may be formed of rubber.

The outer sealing member 170 surrounds the side surface 112 of the main body 110 and is disposed between the upper surface 111 of the main body 110 and the outer holder 160. With the sterilization module 100 mounted on an enclosure, the outer sealing member 170 is located between the upper surface 111 of the main body 110 and one surface of the enclosure or between one surface of the enclosure and the outer holder 160.

The outer sealing member 170 can improve waterproofness of the sterilization module 100 through tight sealing of a gap between the main body 110 and an enclosure with the sterilization module 100 mounted thereon.

Next, other embodiments of the present disclosure will be described. Description of the same components as in the above embodiment will be omitted or briefly given. For details of the same components as in the above embodiment, refer to description given for the above embodiment.

Figure 4:
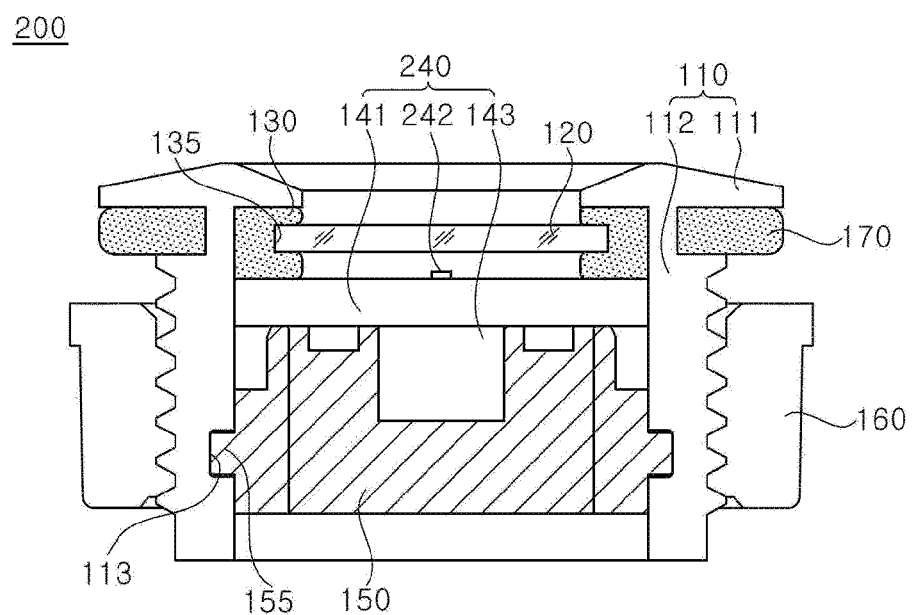
FIG. 4 is an exemplary view of a sterilization module according to a second embodiment of the present disclosure.

FIG. 4 is an exemplary view of a sterilization module according to a second embodiment of the present disclosure.

FIG. 4 is a sectional view of the sterilization module according to the second embodiment of the present disclosure.

The sterilization module 200 according to the second embodiment includes the main body 110, the light-transmissive member 120, the inner sealing member 130, a light emitting module 240, the inner holder 150, and the outer holder 160.

The light emitting module 240 emitting light to the light-transmissive member 120 includes the substrate 141 and a light emitting device 242.

In this embodiment, the light emitting device 242 is a light emitting diode mounted on the substrate 141 by flip-chip mounting. That is, the light emitting device 242 is in chip form, rather than package form. Accordingly, the light emitting device 242 according to this embodiment has a smaller thickness than the light emitting diode package described in the above embodiment.

The sterilization module 200 according to this embodiment can reduce a distance between the light-transmissive member 120 and the substrate 141 since the light emitting device 242 has a smaller thickness than the light emitting diode package. Accordingly, the sterilization module 200 according to this embodiment can be scaled down through reduction in thickness, that is, distance from an upper surface thereof to a lower surface thereof.

Figure 5:
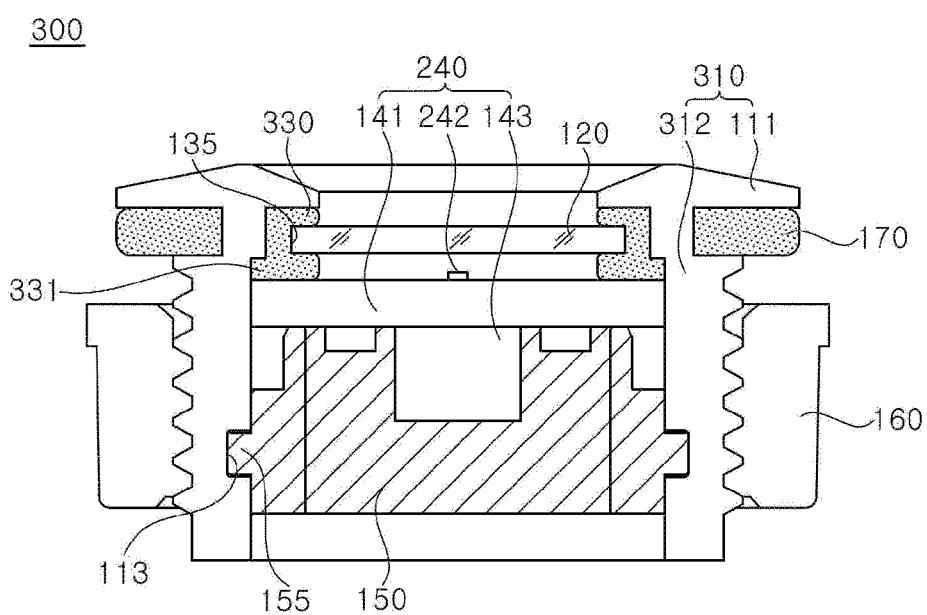
FIG. 5 is an exemplary view of a sterilization module according to a third embodiment of the present disclosure.

FIG. 5 is an exemplary view of a sterilization module according to a third embodiment of the present disclosure.

FIG. 5 is a sectional view of the sterilization module 300 according to the third embodiment of the present disclosure.

Referring to FIG. 5, the sterilization module 300 according to the third embodiment includes the main body 310, the light-transmissive member 120, an inner sealing member 330, the light emitting module 240, the inner holder 150, and the outer holder 160.

The inner sealing member 330 according to this embodiment has a structure in which a part of a lower portion thereof connected to a lower surface thereof protrudes farther outward than an upper portion thereof. That is, the lower surface of the inner sealing member 330, which is held against a substrate 141, is larger in width than an upper surface of the inner sealing member 330, which is held against an upper surface of the main body 310. Here, the width is a distance from an inner side surface of the inner sealing member 330 to an outer side surface of the inner sealing member 330.

In addition, a side surface 312 of the main body 310, which adjoins the inner sealing member 330, has a larger diameter at a lower portion thereof than at an upper portion thereof. Accordingly, a contact area between the main body 310 and the inner sealing member 330 is increased. In addition, a moisture intrusion path between the main body 310 and the inner sealing member 330 is lengthened. Accordingly, it is possible to prevent intrusion of moisture from the outside of the sterilization module 300 into the main body 310 along a gap between the main body 310 and the inner sealing member 330.

In addition, the protrusion 331 formed around a lower outer side surface of the inner sealing member 330 has a small thickness. The protrusion 331 of the inner sealing member 330 has large strain due to small thickness thereof. In addition, since the inner sealing member 330 is formed of an elastic material, the protrusion 331 also has elasticity. Accordingly, the protrusion 331 of the inner sealing member 330 is deformed in the shape of the inner surface of the main body 310 due to large strain thereof and is more firmly held against the inner surface of the main body 310 due to elasticity thereof. That is, the sterilization module 300 according to this embodiment can have improved waterproofness by virtue of the inner sealing member 330 capable of being held against the main body 310 without leaving any gap therebetween.

The substrate 141 of the light emitting module 240 is disposed between the inner sealing member 330 and the inner holder 150. In addition, when fastened to the main body 310, the inner holder 150 upwardly presses the substrate 141 against the inner sealing member 330. As a result, the substrate 141 is secured inside the main body 310 by downward pressing force applied by the inner sealing member 330 located on an upper surface of the substrate 141 and upward pressing force applied by the inner holder 150 located under the substrate 141.

In this embodiment in which the lower surface of the inner sealing member 330 is lager in width than the upper surface of the inner sealing member 330, the inner sealing member 330 can contact the substrate 141 over an increased area, as compared with the above embodiments in which the lower surface of the inner sealing member has the same width as the upper surface of the inner sealing member.

As a contact area between the inner sealing member 330 and the substrate 141 increases, force applied to the substrate 141 by the inner sealing member 330 is distributed more widely. Thus, increase in width of the lower surface of the inner sealing member 330 can reduce downward pressure applied to the substrate 141 by the inner sealing member 330. Accordingly, the sterilization module 300 according to this embodiment can prevent damage to the substrate 141 through reduction in pressure applied to the substrate 141 by the inner sealing member 330.

Figure 6:
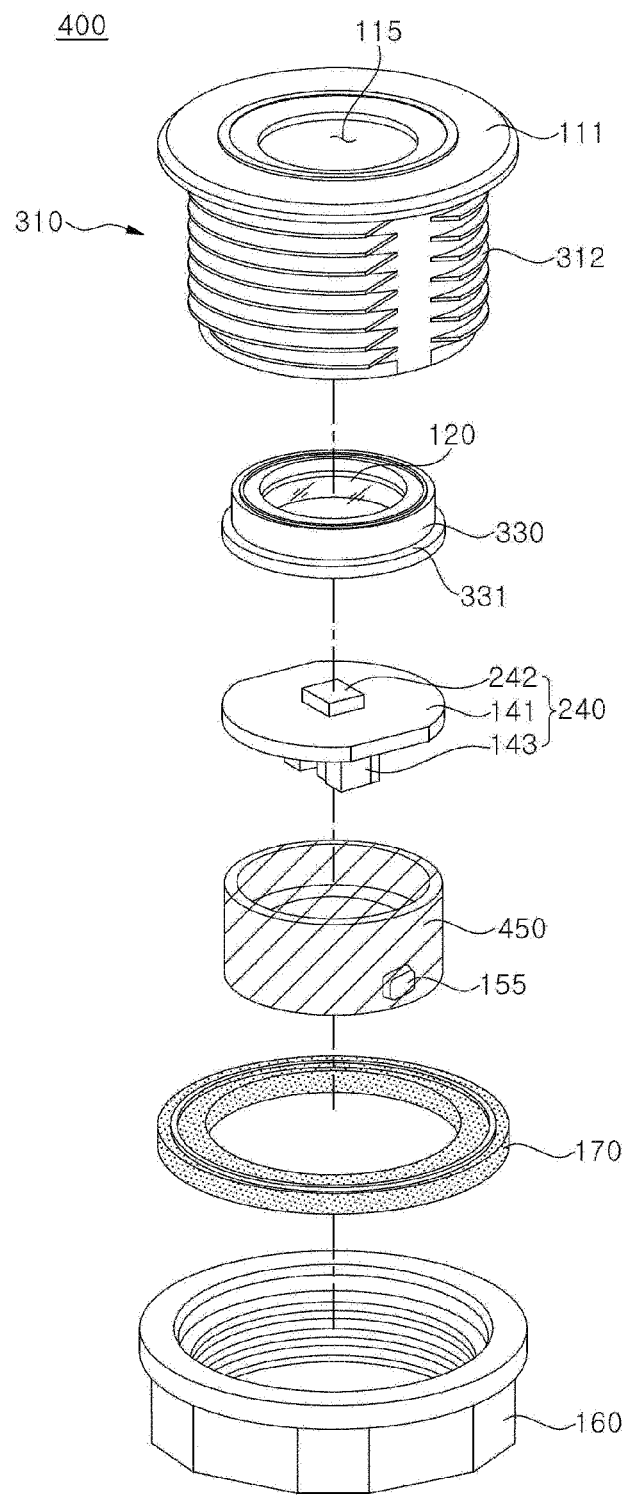
FIG. 6 and FIG. 7 are exemplary views of a sterilization module according to a fourth embodiment of the present disclosure, where.
Figure 7:
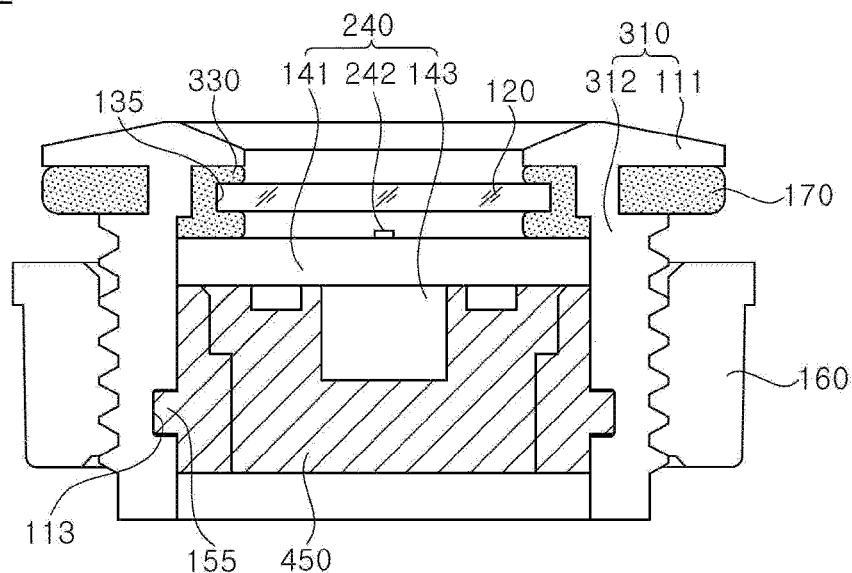

FIG. 6 and FIG. 7 are exemplary views of a sterilization module according to a fourth embodiment of the present disclosure. FIG. 6 is an exploded view of a sterilization module 400 according to the fourth embodiment of the present disclosure. In addition, FIG. 7 is a sectional view of the sterilization module 400 according to the fourth embodiment of the present disclosure.

Referring to FIG. 6 and FIG. 7, the sterilization module 400 according to the fourth embodiment includes a main body 310, the light-transmissive member 120, an inner sealing member 330, the light emitting module 240, an inner holder 450 and the outer holder 160.

Since an upper surface of the inner holder 450 is held against a lower surface of the substrate 141, components 143 mounted on the lower surface of the substrate 141 are located inside the inner holder 450.

The inner holder 450 according to this embodiment has a larger inner diameter at an upper portion thereof than at a lower portion thereof. That is, the inner holder 450 according to this embodiment has a wider space for the components 143 than the inner holders according to the above embodiments.

With this structure of the inner holder 450, the sterilization module 400 according to this embodiment can increase an area of the lower surface of the substrate 141, which is available for mounting the components 143. Accordingly, the sterilization module 400 according to this embodiment can provide easy mounting of the components 143 and enhanced freedom of design through better utilization of the lower surface of the substrate 141.

Figure 8:
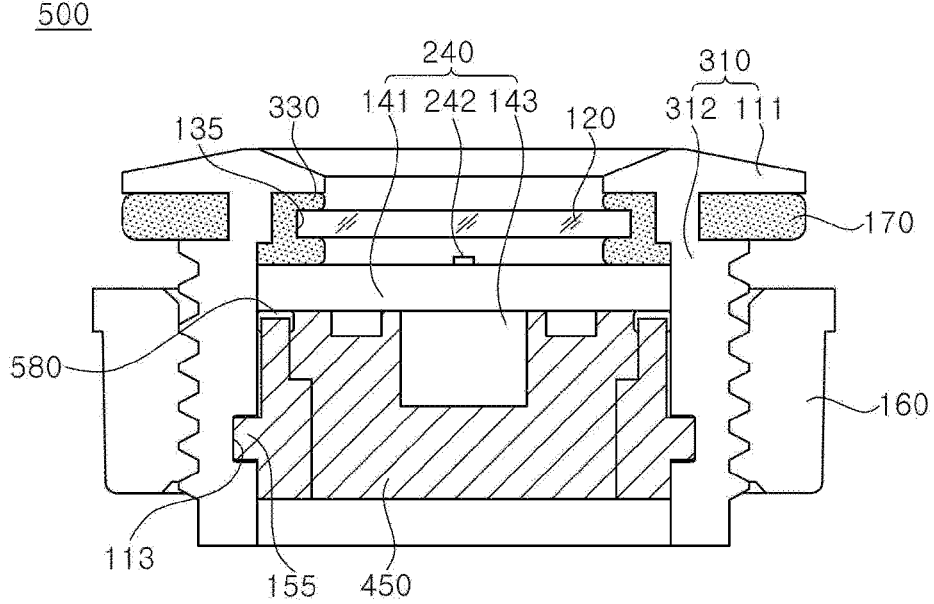
FIG. 8 is an exemplary view of a sterilization module according to a fifth embodiment of the present disclosure.

FIG. 8 is an exemplary view a sterilization module according to a fifth embodiment of the present disclosure.

Referring to FIG. 8, the sterilization module 500 according to the fifth embodiment includes the main body 310, the light-transmissive member 120, the inner sealing member 330, the light emitting module 240, then inner holder 450, a buffer member 580, and the outer holder 160.

The buffer member 580 is formed of an elastic material and covers an upper surface of the inner holder 450. According to this embodiment, due to the presence of the buffer member 580, a lower surface of the substrate 141 contacts the elastic buffer member 580, rather than directly contacting the upper surface of the inner holder 450. Thus, the buffer member 580 can prevent damage to the substrate 141, such as occurrence of scratches on the lower surface of the substrate 141 due to direct pressure applied to the lower surface by the upper surface of the inner holder 450.

Since the upper surface of the inner holder 450 has a narrow width, the inner holder 450 is greatly affected by process factors or errors. That is, during manufacture of the inner holder 450, a structural problem may occur in the upper surface of the inner holder 450 due to process factors or errors.

According to this embodiment, the elastic buffer member 580 covering the upper surface of the inner holder 450 can reduce a problem caused by structural defects of the upper surface of the inner holder 450 due to process errors.

For example, the inner holder 450 can have an excessively narrow upper surface due to process errors. That is, the inner holder 450 can have a pointed upper end. Here, the buffer member 580 covering the upper surface of the inner holder 450 can prevent the substrate 141 from being damaged by the pointed upper end of the inner holder 450.

In addition, the inner holder 450 may have a highly sloped upper surface due to process errors. When the highly sloped upper surface of the inner holder 450 presses the substrate 141, a portion of the substrate 141 held against the upper surface of the inner holder 450 is also sloped in the shape of the upper surface of the inner holder 450. That is, the substrate 141 having a flat structure is partially warped due to the structural defect of the upper surface of the inner holder 450. If pressing force of the inner holder 450 against the substrate 141 is large, the substrate 141 can be broken.

According to the present disclosure, the elastic buffer member 580 covering the upper surface of the inner holder 450 can prevent the substrate 141 from being directly affected by structural defects of the upper surface of the inner holder 450.

Thus, by virtue of the buffer member 580, the sterilization module 500 according to this embodiment can prevent or reduce damage to the substrate 141 due to structural defects of the upper surface of the inner holder 450.

Figure 9:
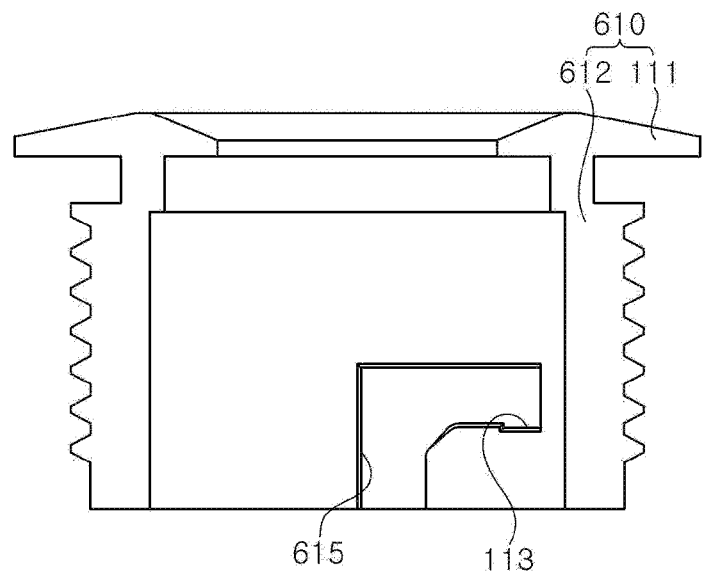
FIG. 9 and FIG. 10 are exemplary views of a sterilization module according to a sixth embodiment of the present disclosure, where.
Figure 10:
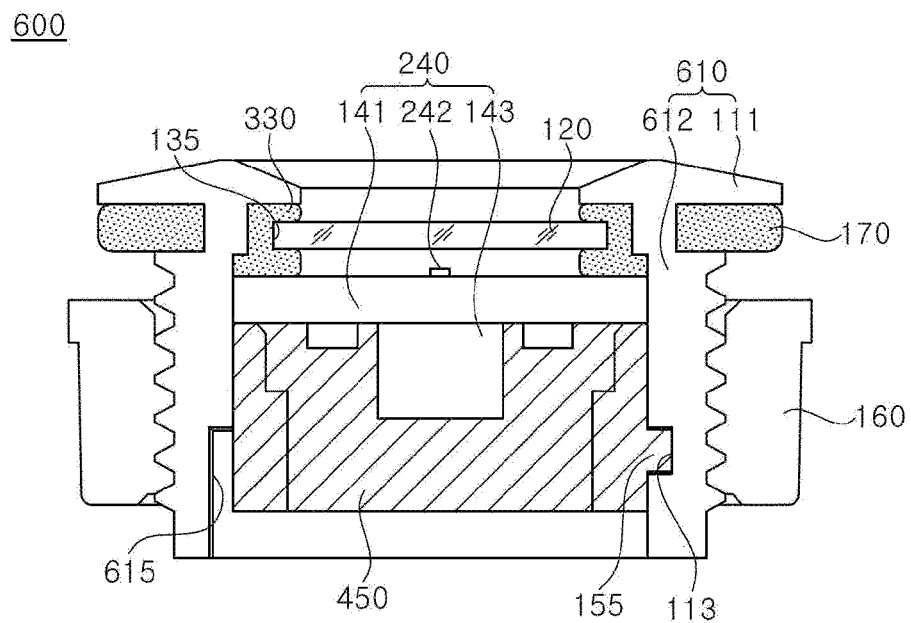
Figure 11:
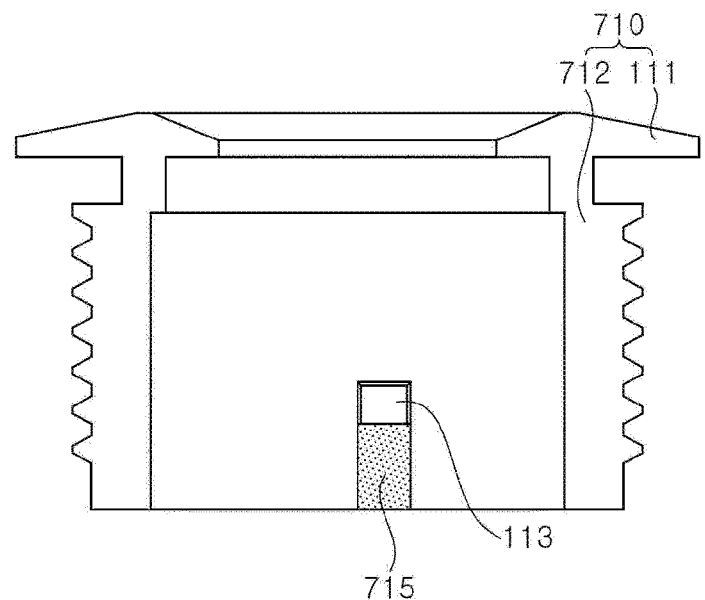
FIG. 11 and FIG. 12 are exemplary views of a sterilization module according to a seventh embodiment of the present disclosure, where.
Figure 12:
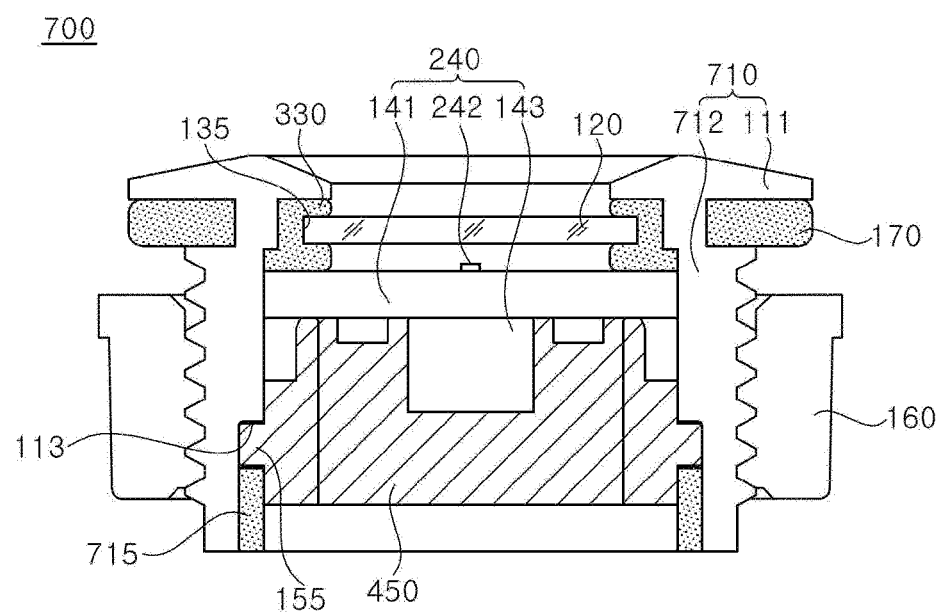

FIG. 9 to FIG. 10 are exemplary views of a sterilization module according to a sixth embodiment of the present disclosure and FIG. 11 to FIG. 12 are exemplary views of a sterilization module according to a seventh embodiment of the present disclosure FIG. 9 is a sectional view of a main body 610 of a sterilization module 600 according to the sixth embodiment and FIG. 10 is a sectional view of the sterilization module 600 according to the sixth embodiment. In addition, FIG. 11 is a sectional view of a main body 710 of a sterilization module 700 according to the seventh embodiment and FIG. 12 is a sectional view of the sterilization module 700 according to the seventh embodiment.

Referring to FIG. 9 to FIG. 12, the sterilization module 600 or 700 according to the sixth or seventh embodiments includes a main body 610 or 710, the light-transmissive member 120 (FIG. 2), the inner sealing member 330 (FIG. 6), the light emitting module 240 (FIG. 6), the inner holder 450 (FIG. 6), and the outer holder 160 (FIG. 2).

According to the sixth and seventh embodiments, the main body 610 or 710 includes a fastening guide 615 or 715 formed on a side surface 612 or 712. As shown in FIG. 9 and FIG. 11, the fastening guide 615 or 715 is formed on an inner side surface of the main body 610 or 710. The fastening guide 615 or 715 extends from a lower surface of the main body 610 or 710 to a fastening groove 113. That is, the fastening guide 615 or 715 is connected at one end thereof to the lower surface of the main body 610 or 710 and is connected at the other end thereof to the fastening groove 113.

In the sixth embodiment, the fastening guide 615 is a groove connecting the lower surface of the main body 610 to the fastening groove 113.

According to this embodiment, the coupling portion 155 of the inner holder 450 is inserted into the fastening guide 615 of the main body 610 and is moved along the fastening guide 615 until the coupling portion 155 is inserted into the fastening groove 113.

Referring to FIG. 9, the fastening guide 615 may have a bent shape. Such a bent shape allows the fastening groove 113 not to be located on a straight line connecting the one end of the fastening guide 615 to the other end of the fastening guide 615, thereby helping the coupling portion 155 of the inner holder 450 to remain inserted into the fastening groove 113. That is, the fastening guide 615 having such a shape can prevent the coupling portion 155 of the inner holder 450 from falling out of the fastening groove 113 due to an external impact and causing separation of the inner holder 450 from the main body 610. Thus, the sterilization module 600 including the fastening guide 615 of FIG. 9 and FIG. 10 can ensure more reliable coupling between the inner holder 450 and the main body 610.

Referring to FIG. 11 and FIG. 12, the fastening guide 715 of the seventh embodiment forms a part of the inner side surface of the main body 710 and is formed of an elastic material.

According to this embodiment, the inner holder 450 is inserted into the main body 710 with the coupling portion 155 of the inner holder 450 located on the fastening guide 715 of the main body 710. Upon inserting the inner holder 450 into the main body 710, the coupling portion 155 presses the fastening guide 715 and a portion of the fastening guide 715 pressed by the coupling portion 155 is compressed. That is, the fastening guide 715 is compressed against the coupling portion 155 to receive the coupling portion 155 therein. That is, the inner holder 450 is moved to the fastening groove 113 inside the main body 710 while compressing the fastening guide 715 with the coupling portion 155. Since the fastening guide 715 has elasticity, a portion of the fastening guide 715 compressed by the coupling portion 155 is returned to an original shape thereof as soon as the coupling portion 155 leaves the portion. Accordingly, when the coupling portion 155 is located in the fastening groove 113, the fastening guide 715 is completely restored to an original shape thereof.

A lower surface of the fastening groove 113 corresponds to an upper surface of the fastening guide 715. Accordingly, the lower surface of the fastening groove 113, which has been compressed by the coupling portion 155 of the inner holder 450, is returned to an original shape thereof as soon as the coupling portion 155 is inserted into the fastening groove 113. That is, the lower surface of the fastening groove 113 is returned to the original shape thereof, in which the lower surface of the fastening groove 113 protrudes from a side surface of the fastening groove 113 towards the inside of the main body 710. When returned to the original shape thereof, the lower surface of the fastening groove 113 prevents the coupling portion 155 from being separated from the fastening groove 113.

For example, the inner holder 450 may include a pair of coupling portions 155 protruding in opposite directions. In addition, the main body 610 or 710 may include a pair of fastening grooves 113 facing each other.

Here, a distance between respective tips of the pair of coupling portions 155 is greater than an inner diameter of the main body 610 or 710 at a location under the fastening grooves 113 and is less than or equal to a distance between respective inner side surfaces of the pair of fastening grooves 113.

Accordingly, it is difficult to insert/couple the inner holder 450 into/to the main body 610 or 710 without a separate structural feature. In addition, the inner holder 450 or the main body 610 or 710 can be damaged during insertion/coupling of the inner holder 450 into/to the main body 610 or 710. In order to facilitate damage-free insertion of the inner holder 450 into the main body 610 or 710, the main body 610 or 710 needs to be stretchable. In addition, in order to allow the inner holder 450 to remain inserted into the main body 610 or 710, the coupling portion 155 should not be separated from the fastening groove 133.

With the fastening guide 615 or 715 formed on the inner side surface of the main body 610 or 710, the sterilization module 600 or 700 according to the sixth or seventh embodiment can facilitate movement of the coupling portion 155 of the inner holder 450 to the fastening groove 113. Accordingly, the sterilization module 600 or 700 according to the sixth or seventh embodiment can ensure easy assembly by virtue of the fastening guide 615 or 715. In addition, the sterilization module 600 or 700 according to the sixth or seventh embodiment allows a material for the main body 610 or 710 not to be limited to resilient materials through elimination of the need for the main body 610 or 710 to be stretched upon inserting the inner holder 450 along the fastening guide 615 or 715. Further, the sterilization module 600 or 700 according to the sixth or seventh embodiment can prevent damage to the main body 610 or 710 or the inner holder 450 during coupling of the main body 610 or 710 to the inner holder 450.

Although some embodiments have been described herein, it should be understood that these embodiments are provided for illustration only and are not to be construed in any way as limiting the present disclosure. The scope of the present disclosure should be defined by the appended claims and equivalents thereto.

What is claimed is:

1. A sterilization module comprising:
a main body comprising an opening formed through an upper surface thereof;
a light-transmissive member disposed inside the main body to cover the opening and transmitting light therethrough;
an inner sealing member surrounding a side surface of the light-transmissive member and formed of an elastic material;
a light emitting module comprising a substrate and a light emitting device mounted on an upper surface of the substrate, the light emitting module emitting light to the light-transmissive member; and
an inner holder fastened to an inner side surface of the main body and holding the light emitting module inside the main body,
wherein the inner sealing member has an upper surface held against the upper surface of the main body and a lower surface held against an upper surface of the substrate of the light emitting module, and
the light-transmissive member is spaced apart from the substrate by a predetermined distance which allows an irradiance of light emitted to an outside of the sterilization module through the light-transmissive member to be 65% or more of an irradiance of light emitted from the light emitting device.

2. The sterilization module according to claim 1, further comprising:
a fastening groove formed on the inner side surface of the main body; and
a coupling portion formed on an outer side surface of the inner holder,
wherein the inner holder is fastened and secured to the main body through insertion of the coupling portion into the fastening groove.

3. The sterilization module according to claim 2, wherein:
the main body further comprises a groove-shaped fastening guide formed on a portion of the inner side surface thereof, the groove-shaped fastening guide being connected at one end thereof to a lower surface of the main body and connected at the other end thereof to the fastening groove; and
the coupling portion of the inner holder is inserted into the fastening guide of the main body and is moved along the fastening guide until the coupling portion is inserted into the fastening groove.

4. The sterilization module according to claim 2, wherein:
the main body further comprises a fastening guide formed on a portion of the inner side surface thereof and having elasticity, the fastening guide being connected at one end thereof to a lower surface of the main body and connected at the other end thereof to the fastening groove; and
the coupling portion of the inner holder is moved along the fastening guide until the coupling portion is inserted into the fastening groove.

5. The sterilization module according to claim 2, wherein a distance from an inner upper surface of the main body to an upper end of the fastening groove is less than a sum of:
a height of the inner sealing member,
a thickness of the substrate, and
a distance from an upper surface of the inner holder to an upper end of the coupling portion.

6. The sterilization module according to claim 1, wherein:
an upper surface of the inner holder has a smaller area than an area of a lower surface of the inner holder; and the upper surface of the inner holder faces a lower surface of the substrate.

7. The sterilization module according to claim 6, further comprising:
 a buffer member covering the upper surface of the inner holder.

8. The sterilization module according to claim 1, wherein:
 the inner sealing member further comprises a protrusion formed around an outer surface thereof;
 the main body further comprises an insertion groove formed around the inner side surface thereof; and
 the protrusion of the inner sealing member is inserted into the insertion groove of the main body.

\* \* \* \* \*